(12) United States Patent
Ko et al.

(10) Patent No.: US 8,801,729 B2
(45) Date of Patent: Aug. 12, 2014

(54) APPARATUS AND METHOD FOR SUBCUTANEOUS ELECTRODE INSERTION

(75) Inventors: Michael Ko, Mission Viejo, CA (US); Duane Tumlinson, San Clemente, CA (US)

(73) Assignee: Cameron Health, Inc., St. Paul, MN (US)

( * ) Notice: Subject to any disclaimer, the term of this patent is extended or adjusted under 35 U.S.C. 154(b) by 172 days.

(21) Appl. No.: 13/436,438

(22) Filed: Mar. 30, 2012

(65) Prior Publication Data

US 2012/0191106 A1    Jul. 26, 2012

Related U.S. Application Data

(63) Continuation of application No. 12/698,627, filed on Feb. 2, 2010, now Pat. No. 8,157,813, which is a continuation of application No. 11/006,291, filed on Dec. 6, 2004, now Pat. No. 7,655,014.

(51) Int. Cl.
*A61B 19/00* (2006.01)
(52) U.S. Cl.
USPC .......................................................... 606/129
(58) Field of Classification Search
USPC ................................................. 606/129, 148
See application file for complete search history.

(56) References Cited

U.S. PATENT DOCUMENTS

| | | | |
|---|---|---|---|
| 4,011,657 A * | 3/1977 | Vance .............................. 30/337 |
| 5,215,527 A * | 6/1993 | Beck et al. ............... 604/164.09 |
| 5,443,492 A | 8/1995 | Stokes et al. |
| 7,566,318 B2 * | 7/2009 | Haefner ........................... 604/22 |
| 7,655,014 B2 | 2/2010 | Ko et al. |
| 8,157,813 B2 | 4/2012 | Ko et al. |
| 2002/0082658 A1 | 6/2002 | Heinrich et al. |
| 2004/0186529 A1 | 9/2004 | Bardy et al. |
| 2004/0260370 A1 * | 12/2004 | Ley et al. ....................... 607/115 |

FOREIGN PATENT DOCUMENTS

| | | |
|---|---|---|
| AU | 2005314611 | 6/2011 |
| JP | 4943343 | 5/2012 |

OTHER PUBLICATIONS

"U.S. Appl. No. 11/006,291, Advisory Action mailed Jul. 10, 2009", 3 pgs.
"U.S. Appl. No. 11/006,291, Final Office Action mailed Apr. 20, 2009", 7 pgs.
"U.S. Appl. No. 11/006,291, Non Final Office Action mailed Aug. 27, 2008", 7 pgs.

(Continued)

*Primary Examiner* — Katherine Dowe
*Assistant Examiner* — Michael Mendoza
(74) *Attorney, Agent, or Firm* — Schwegman, Lundberg & Woessner, P.A.

(57) ABSTRACT

Devices and methods for electrode implantation. A first embodiment includes an electrode insertion tool adapted to tunnel through tissue and attach, at its distal end, to a lead, such that the lead may be pulled into the tunneled space as the electrode insertion tool is removed. Additional embodiments include methods for inserting electrode/lead assemblies, including a method wherein an insertion tool is first used to tunnel through tissue, then to pull an electrode/lead into the tunneled space. In a further embodiment the insertion tool is next used, with a splittable sheath disposed thereon, to create an additional path into tissue, after which the insertion tool is removed, leaving the sheath in place; a lead is inserted to the sheath, and, finally, the splittable sheath is removed over the lead.

5 Claims, 22 Drawing Sheets

(56) References Cited

OTHER PUBLICATIONS

"U.S. Appl. No. 11/006,291, Notice of Allowance mailed Oct. 21, 2009", 8 pgs.

"U.S. Appl. No. 11/006,291, Response filed May 2, 2008 to Restriction Requirement mailed Apr. 4, 2008", 9 pgs.

"U.S. Appl. No. 11/006,291, Response filed Jun. 19, 2009 to Final Office Action mailed Apr. 20, 2009", 11 pgs.

"U.S. Appl. No. 11/006,291, Response filed Jul. 20, 2009 to Final Office Action mailed Apr. 20, 2009", 11 pgs.

"U.S. Appl. No. 11/006,291, Response filed Dec. 24, 2008 to Non Final Office Action mailed Aug. 27, 2008", 11 pgs.

"U.S. Appl. No. 11/006,291, Restriction Requirement mailed Apr. 4, 2008", 7 pgs.

"U.S. Appl. No. 12/698,627, Applicant's Summary of Examiner Interview filed Dec. 16, 2011", 1 pg.

"U.S. Appl. No. 12/698,627, Notice of Allowance mailed Jan. 3, 2012", 9 pgs.

"Australian Application Serial No. 2011202081, First Examiner Report mailed Sep. 28, 2012", 2 pgs.

"Australian Application Serial No. 2011202081, Response filed Jan. 30, 2013 to First Examiner Report mailed Sep. 28, 2012", 2 pgs.

"European Application Serial No. 05810131.2, Office Action mailed Jul. 18, 2008", 4 pgs.

"European Application Serial No. 05810131.2, Office Action mailed Jul. 19, 2007", 2 pgs.

"European Application Serial No. 05810131.2, Office Action mailed Oct. 23, 2007", 3 pgs.

"European Application Serial No. 05810131.2, Response filed Feb. 29, 2008 to Office Action mailed Oct. 23, 2007", 3 pgs.

"European Application Serial No. 05810131.2, Response filed Nov. 27, 2008 to Office Action mailed Jul. 18, 2008", 11 pgs.

"International Application Serial No. PCT/US2005/037759, International Preliminary Report on Patentability mailed Jun. 13, 2007", 7 pgs.

"International Application Serial No. PCT/US2005/037759, International Search Report mailed Feb. 23, 2006", 4 pgs.

"International Application Serial No. PCT/US2005/037759, Written Opinion mailed Feb. 23, 2006", 6 pgs.

\* cited by examiner

Figure 7
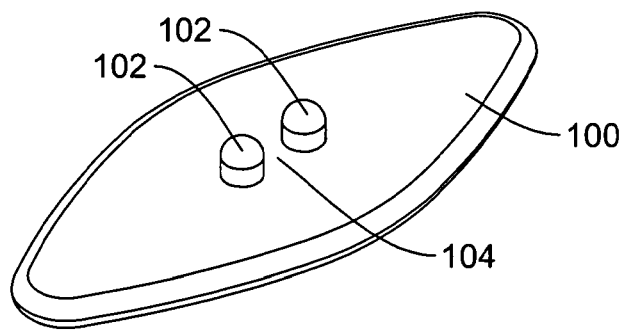
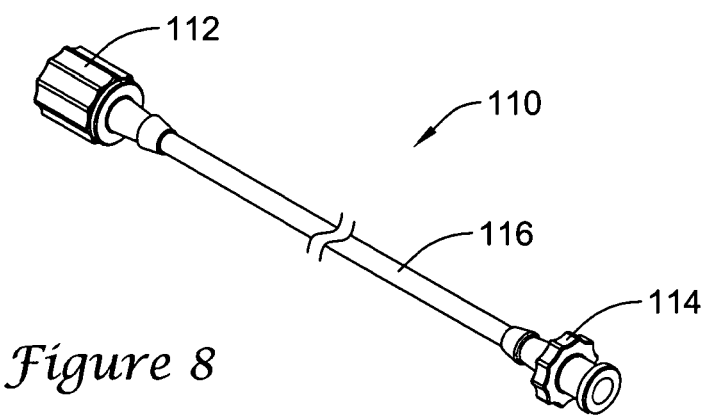
Figure 8

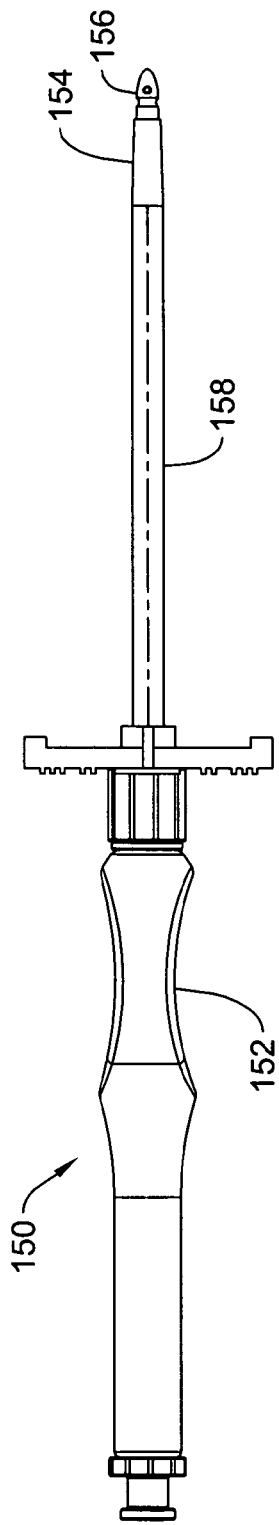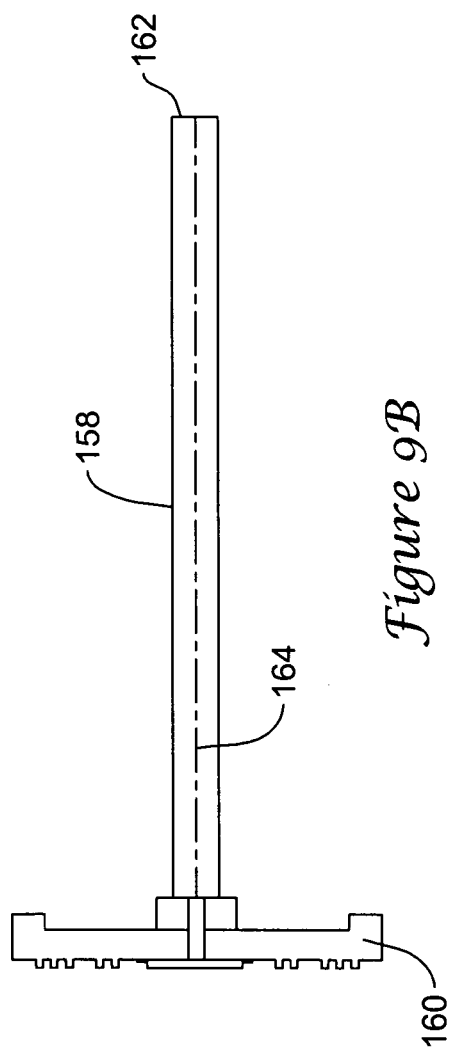
Figure 9A
Figure 9B

APPARATUS AND METHOD FOR SUBCUTANEOUS ELECTRODE INSERTION

RELATED APPLICATIONS

This application is a continuation of U.S. patent application Ser. No. 12/698,627, filed Feb. 2, 2010, published as US 2010-0137879 A1, and titled APPARATUS AND METHOD FOR SUBCUTANEOUS ELECTRODE INSERTION, now U.S. Pat. No. 8,157,813, which is a continuation of U.S. patent application Ser. No. 11/006,291, filed Dec. 6, 2004, now U.S. Pat. No. 7,655,014 and titled APPARATUS AND METHOD FOR SUBCUTANEOUS ELECTRODE INSERTION, the entire disclosure of which is Incorporated herein by reference.

FIELD

The present invention is related to the field of medical treatments including electrode implantations. More particularly, the present invention is related to the field of electrode implantation or insertion for cardiac treatments.

BACKGROUND

The use of implantable pacing and defibrillation devices to treat or prevent various cardiac problems has become relatively widespread. Several difficulties with such treatments relate to placement and durability of electrodes. Typically, well practiced, careful and gentle maneuvers are required during insertion to avoid breaking the leads and/or electrodes. Once placed, leads may fracture after being subjected to repeated stresses as the heart beats and the patient moves. Leads and electrodes may also migrate from their desired position.

For transvenous implantation, a lead is typically introduced by advancing it through a vein to a location in or near the heart with the aid of fluoroscopy. The lead is then anchored to heart tissue or a passive anchor mechanism, such as a tine, is utilized to prevent the lead from moving. The heart tissue will tend to form around the lead, attenuating sensed signals as well as altering pacing and/or defibrillating thresholds. Because implantation requires traversing the vasculature as well as placement and anchoring within the heart, many problems can arise.

Many lead insertion techniques push a lead into place into tissue or through the vasculature. Pushing the lead stresses the lead and can cause lead failure. With vascular implantations, the pathway is defined but is subject to constrictions and tight turns. Non-vascular implantation calls for tunneling through existing tissue. While extra stiffness may help with lead insertion and aid accurate lead placement, stiffer leads create their own problems with migration, perforation, and fracture. As stiffness increases, the ability of the lead to inadvertently perforate tissue rises. Further, with extra stiffness, the lead does not rest in place during muscle movement, tending to increase the size of any associated fibroid, and potentially leading to migration.

SUMMARY

The present invention, in a first embodiment, includes a tool for implanting a lead electrode assembly. The tool may include a handle and a relatively stiff shaft having a proximal end and a distal end, with the handle secured to the proximal end of the shaft. The distal end of the shaft includes an attachment feature which can be used to attach to a lead electrode assembly. The attachment feature, in use, allows the tool to be secured to the lead electrode assembly after it is advanced through tissue. Once so secured, the tool enables pulling or pushing of the lead electrode assembly through the portion of tissue that has already been tunneled by the tool.

The shaft may also define a lumen extending distally from a port or hub (such as a Luer hub) in the handle. The shaft may then include a fluid infusion port for infusing a fluid forced through the lumen into tissue during an implantation procedure. In an illustrative method embodiment, the fluid infusion port and lumen are used to infuse a local anesthetic such as lidocaine during an implantation.

The attachment feature may take the form of a suture hole allowing a suture to be passed therethrough. In a preferred embodiment, the fluid infusion port opens into a suture hole. The shaft may be straight, may include a curve, or may define an arc of curvature. In one embodiment, the shaft is provided with a curvature that mimics the curvature of a patient's lower ribcage. The shaft may also be shapeable such that a user can adapt the shaft to the shape of a selected portion of anatomy such as a patient's ribcage.

In another embodiment, an electrode insertion tool kit is provided, the tool kit including a tool for inserting an electrode and a splittable sheath for use in conjunction with the tool. The tool may have one or more of the features noted above. The splittable sheath is preferably sized to snugly fit over the tool. The kit may also include more than one insertion tool, one being straight and one having a curved shape, as well as an infusion tubing set for coupling to the one or more insertion tools, and a shaping tool for re-shaping or modifying the shape of an insertion tool.

Further embodiments include methods for inserting electrodes and leads to a patient subcutaneously. In one such embodiment, first and second incisions are made at spaced apart locations. An insertion tool having proximal and distal ends is inserted via the first incision and advanced subcutaneously toward the second incision. The distal end of the insertion tool may be passed out through the second incision. An electrode/lead assembly is then attached to the distal end of the insertion tool, and the insertion tool is withdrawn via the same path it was inserted through. As the insertion tool is withdrawn, the electrode/lead assembly is pulled subcutaneously into the patient. An alternative embodiment does not include passing the distal end of the insertion tool out of the second incision, instead only passing the distal end proximate the incision such that the electrode/lead assembly may be attached thereto.

In a further embodiment, the insertion tool is completely withdrawn through the first incision until the portion of the electrode/lead assembly connected to the insertion tool is pulled through the first incision. Then the insertion tool is inserted via the first incision and advanced subcutaneously in a direction different from the direction of the second incision. Preferably, the insertion tool is advanced in a direction that is at a significant angle with respect to a line along which the first and second incisions lie. The insertion tool is then removed and the electrode/lead assembly advanced through the path defined by the insertion tool.

In yet a further embodiment, the insertion tool, at least during the second insertion through the first incision, is inserted with a sheath placed thereover. Once the insertion tool and sheath are inserted to a desired extent, the insertion tool is removed, leaving the sheath in place. Then the electrode/lead assembly is inserted into the sheath to a desired extent. Finally, the sheath is removed. Preferably the sheath includes a line of axial weakness, or is a splittable sheath, so

BRIEF DESCRIPTION OF THE DRAWINGS

FIG. 7 shows a perspective view of an insertion tool bending device;

FIG. 8 shows a perspective partial view of an infusion tubing set;

FIGS. 9A-9B show, in combination and alone, an insertion tool with a splittable sheath and a splittable sheath by itself;

DETAILED DESCRIPTION

The following detailed description should be read with reference to the drawings. The drawings, which are not necessarily to scale, depict illustrative embodiments and are not intended to limit the scope of the invention.

It should be noted that the terms "lead" and "lead electrode assembly" as used herein carry distinct meanings, with a lead electrode assembly being a lead and electrode coupled together. U.S. patent application Ser. No. 09/940,377 to Bardy et al., now U.S. Pat. No. 6,866,044, is incorporated herein by reference. Bardy et al. suggest several methods for insertion of a defibrillator device including a subcutaneous canister and electrode(s), and explain additional details of subcutaneous defibrillation devices and methods.

Figure 1:
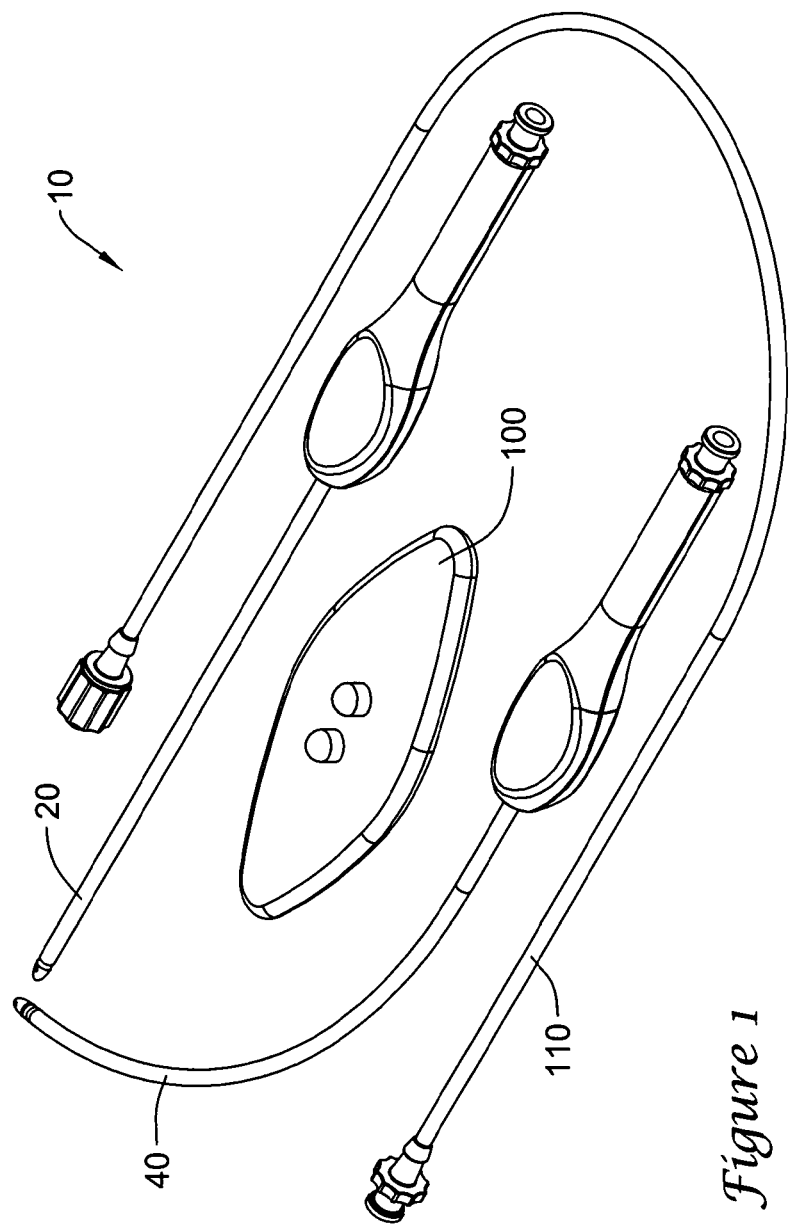
FIG. 1 illustrates in perspective view an electrode insertion tool kit including several components.

FIG. 1 illustrates in perspective view a lead electrode assembly insertion tool kit including several components. The kit 10 includes a number of items, including a straight insertion tool 20, a curved insertion tool 40, a bending tool 100 and an infusion tubing set 110. The kit 10 may further include a splittable sheath (not shown) such as that illustrated in FIGS. 9A-9B. In several illustrative embodiments, the insertion tools 20, 40 include elongate shafts made of stainless steel tubes, with plastic handles, although other materials may be used as desired for either portion. The infusion tubing set 110 will often include a flexible polymeric tubular member, although this is not required. The bending tool 100 may be used to adjust the shape of the insertion tools 20, 40, although again this is not required. Features of each of these elements are further explained below.

Figure 2A:
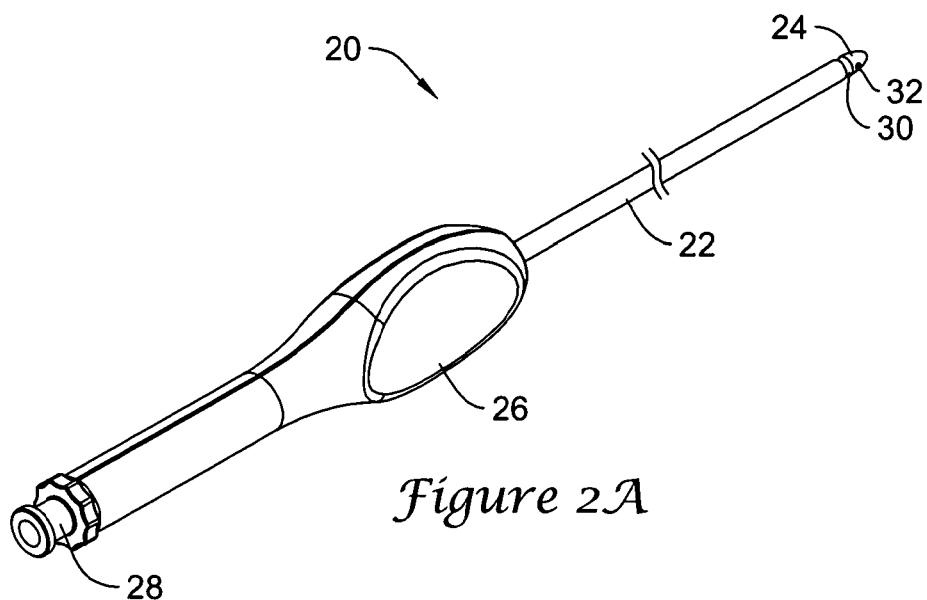
FIGS. 2A-2B show, in perspective and section views, a straight electrode insertion tool.
Figure 2B:
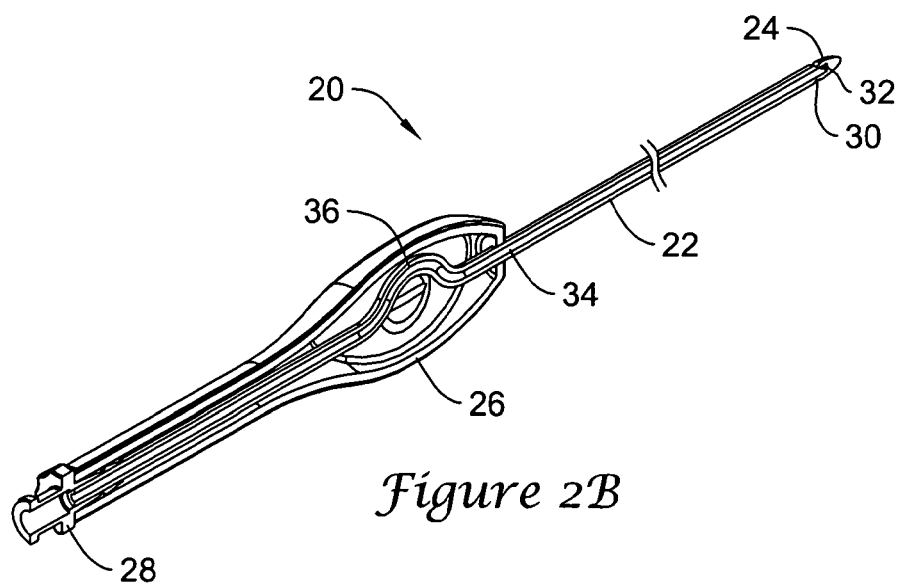

FIGS. 2A-2B show, in perspective and section views, a straight electrode insertion tool. Referring to FIG. 2A, the tool 20 is generally straight distal of its handle 26, and includes a shaft portion 22 that is preferably stiff enough to provide pushability to a distal end 24 for creating a path through tissue. In several embodiments, a relatively rigid metallic member, such as a stainless steel shaft, is used for the shaft portion 22. The shaft 22 is secured to a handle 26 near its proximal end, where a Luer connector 28 is provided.

The distal end 24 of the shaft 22 illustrates a number of attachment features, including a groove 30 and a suture hole 32. For example, the groove 30 may be a radial groove allowing for slipknot attachment to a thread such as a suture. The suture hole 32 may allow for a thread or suture to be passed therethrough and then tied. The end of the tool might also possess specific geometries for attachment to specific electrode designs.

Referring to FIG. 2B, the tool 20 is shown in a cut-away or section view, with the shaft 22 extending through the handle 26. The shaft 22 defines a lumen 34 that extends from the Luer connector 28 to an infusion port opening into the suture hole 32. The handle 26 may be secured to the shaft 22 in any suitable manner, for example, with adhesives, mechanical securing devices (i.e., mating threads, notches, or the like), heat welding, or by overmolding the handle 26 onto the shaft 22. One way to provide additional mechanical strength to any such attachment is to include an offset bend 36 in the shaft 22 under the handle 26.

Figure 3A:
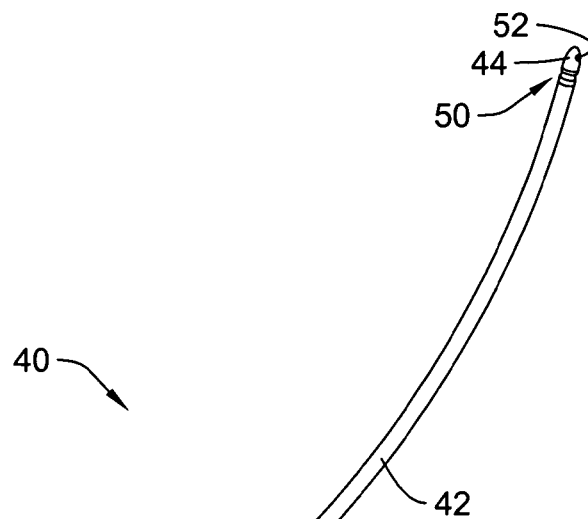
FIGS. 3A-3B show, in perspective and section views, a curved electrode insertion tool.
Figure 3B:
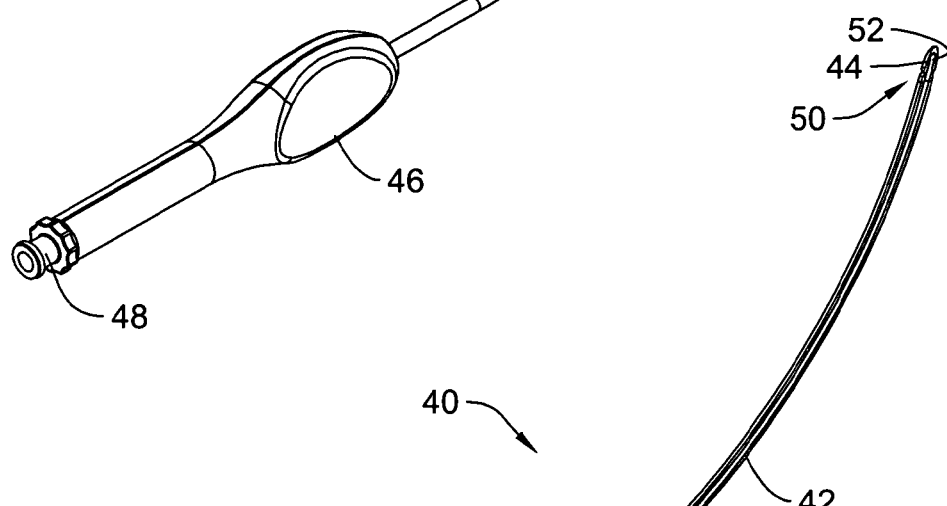

FIGS. 3A-3B show, in perspective and section views, a curved electrode insertion tool. The features are generally similar to those of FIGS. 2A-2B. Referring to FIG. 3A, the tool 40 has a gradual or smooth curve which may be selected or shaped to match a patient's anatomy. In particular, in preferred embodiments, the curve is chosen to correspond to the curvature of a patient's rib, allowing less traumatic passage through the subcutaneous space of a patient along the patient's chest.

The tool 40 includes a shaft portion 42 that is preferably stiff enough to provide pushability to a distal end 44 for creating a path through tissue. In several embodiments, a relatively rigid metallic member, such as a stainless steel shaft, is used for the shaft portion 42. The shaft 42 is secured to a handle 46 near its proximal end, where a Luer connector 48 is provided. Instead of a metallic member, a pushable polymeric member may be used, or, alternatively, a braided shaft member including polymeric layers and a braided support structure.

The distal end 44 of the shaft 42 illustrates a couple of attachment features, including a groove 50 and a suture hole 52. For example, the groove 50 may be a radial groove allowing for slipknot attachment to a thread such as a suture. The suture hole 52 may allow for a thread or suture to be passed therethrough and then tied. In another embodiment, a staple may pass through the hole 52 such that, rather than having a person physically tie or knot a suture, a surgical stapler may be used instead.

Referring to FIG. 3B, the tool 40 is shown in section or cut-away view with the shaft 42 extending through the handle 46. The shaft 42 defines a lumen 54 that extends from the Luer connector 48 to an infusion port opening into the suture hole 52. The handle 46 may be secured to shaft 42 in any suitable way, for example, with adhesives, mechanical securing devices (i.e., threads, notches, or the like), heat welding, or by overmolding the handle 46 onto the shaft 42. One way to improve the mechanical strength of the bond is to include an offset bend 56 in the shaft 42 under the handle 46.

Figure 4A:
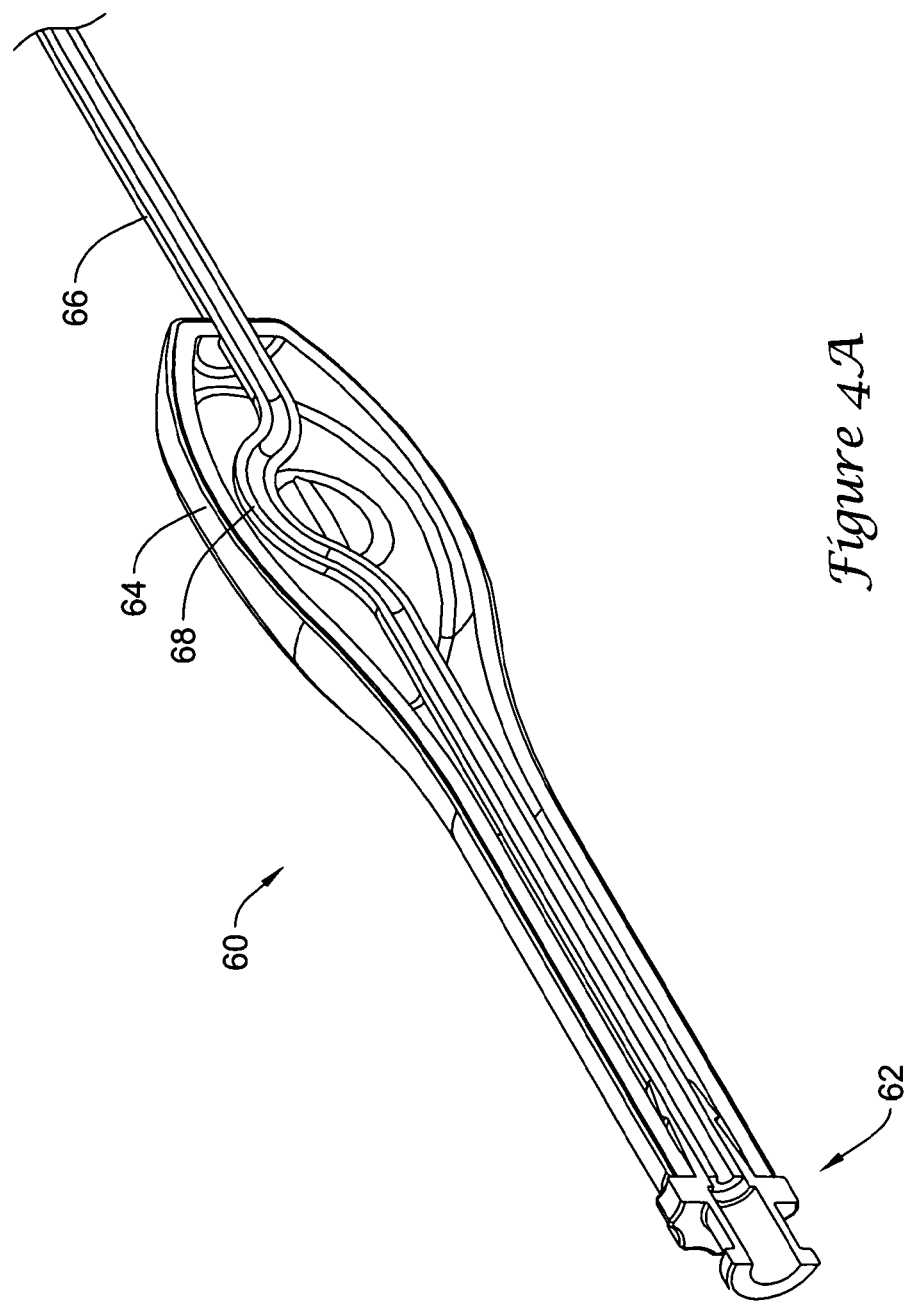
FIGS. 4A-4C show detailed section views of an electrode insertion tool handle.
Figure 4B:
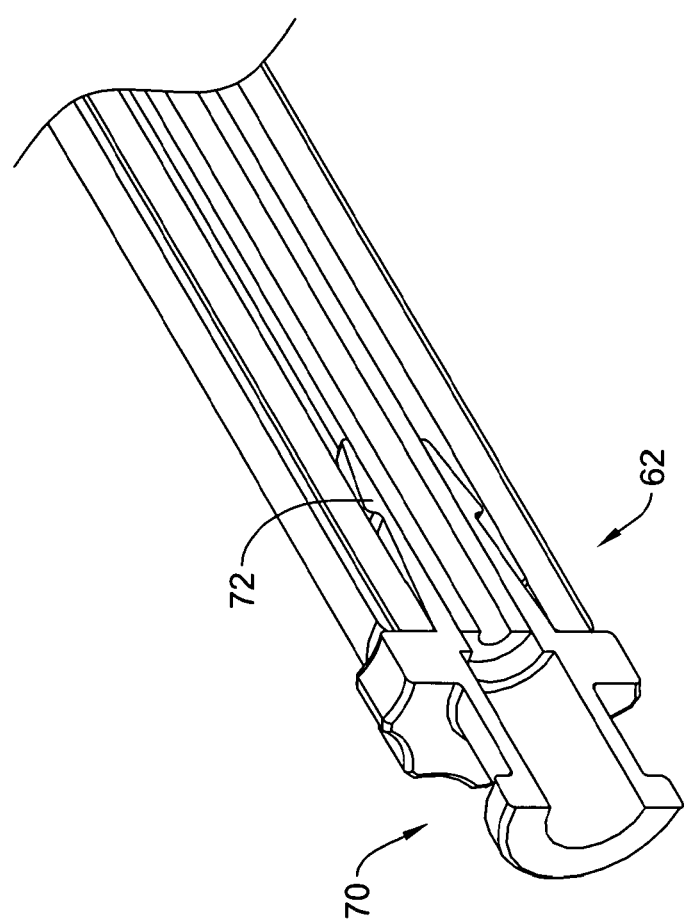
Figure 4C:
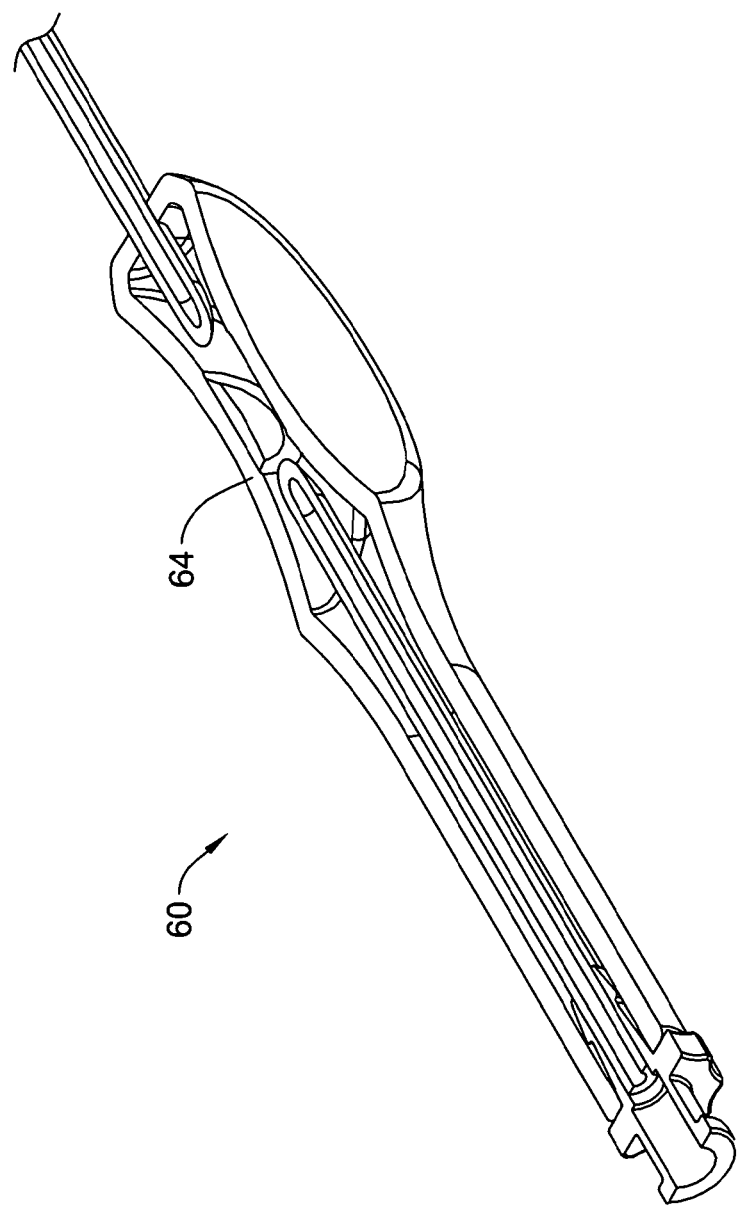

FIGS. 4A-4C show detailed section views of an electrode insertion tool handle. The electrode insertion tool handle 60 may correspond to the handles 26, 46 illustrated in FIGS. 2A-2B and 3A-3B. The handle 60 includes a Luer port 62 for providing access to a lumen defined by the shaft 66. As shown in FIG. 4B, the Luer port/valve 62 includes a proximal securing portion 70 for securing to, for example, a fluid infusion device, and a distal securing portion 72 for securing to the shaft 66.

In an illustrative example, a local anesthetic such as lidocaine may be infused. Other anesthetics, anti-infection drugs, or drugs designed/chosen to prevent or limit swelling or other tissue injury responses may be infused as well. An advantage of providing a medication limiting tissue injury response may be to limit the size of any tissue growth around an implanted lead. Alternatively, for example to ensure good anchoring of a lead, a substance designed to cause or maximize local tissue injury response may be provided. Additionally, certain tissue adhesives could also be delivered through the lumen.

The main handle portion 64, as seen in FIGS. 4A and 4C may be designed to have a flattened side and a wider side. This design aids a doctor/practitioner in grasping the device during tunneling and pulling with the shaft 66, as well as providing space for the offset bend 68 shown in FIG. 4A. The offset bend 68 of the shaft 66 aids in anchoring the shaft 66 in the main handle portion 64. Other handle designs may be used in accordance with the present invention.

Figure 5B:
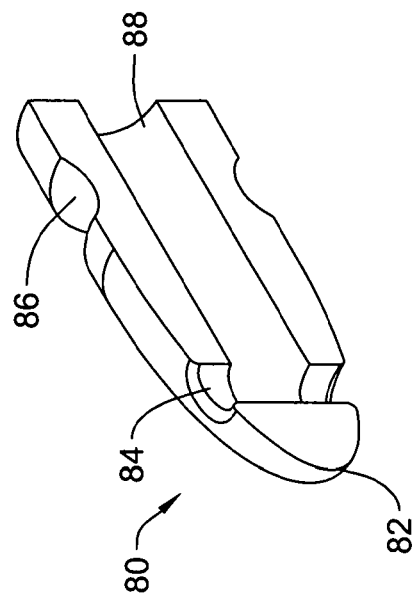
FIGS. 5A-5B show, in perspective and section views, details of an electrode insertion tool tip.
Figure 5A:
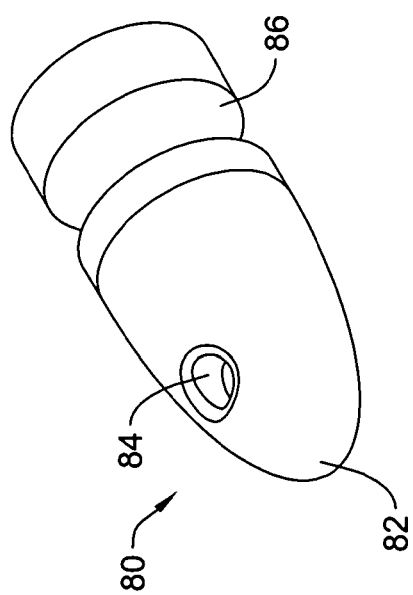

FIGS. 5A-5B show, in perspective and section views, details of an electrode insertion tool tip. The tip 80 may correspond to the distal ends 24, 44 illustrated in FIGS. 2A-2B and 3A-3B. The tip 80 includes a rounded end 82 which may have a "bullet" shape for tunneling between tissue layers while avoiding tunneling through tissue layers. In a preferred embodiment, the rounded end 82 is tapered to allow tunneling into fatty subcutaneous tissue without perforating the skin. Also included are two illustrative attachment features, including a suture hole 84 and a radial groove 86 allowing for suture attachment using, for example, a slipknot.

The tip 80 with end 82, suture hole 84 and groove 86 is also shown in FIG. 5B. Also shown in FIG. 5B is a lumen 88 that terminates in an infusion port that opens laterally through the suture hole 84. With this structure, the suture hole 84 serves two functions, both as an attachment feature and as an extension of the infusion port. The lumen 88 extends through the rest of the shaft (not shown) to a handle and Luer valve such as those shown in FIGS. 2A-2B and 3A-3B.

Figure 6A:
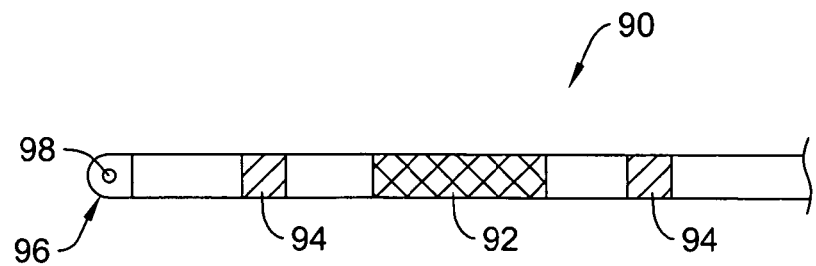
FIGS. 6A-6C show perspective and alternative detail views of a lead electrode assembly.
Figure 6B:
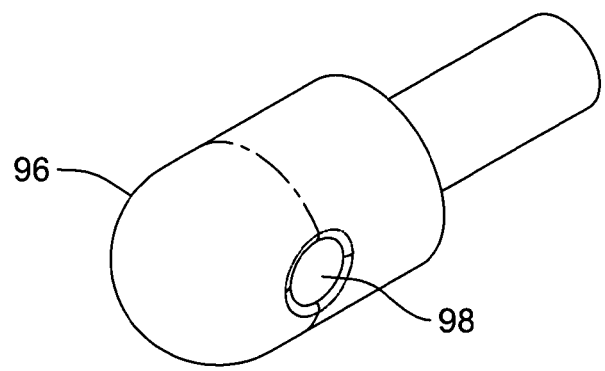
Figure 6C:
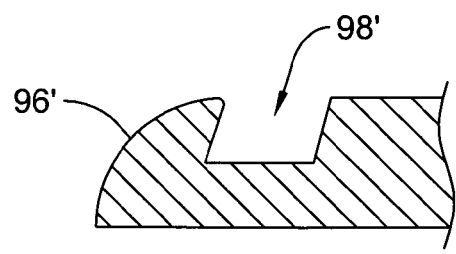

FIGS. 6A-6C show perspective and alternative detail views of a lead electrode assembly. The lead electrode assembly 90 is shown as having a number of electrodes, including a coil electrode 92 and two sense electrodes 94. The assembly 90 has a distal tip 96. As shown in FIG. 6A and further illustrated in FIG. 6B, the distal tip 96 may include a suture hole 98, although any other attachment feature may be used, such as a radial groove as shown in FIGS. 5A-5B or a hook/notch 98' as shown in FIG. 6C in association with tip 96'. For a radial groove 86 or a hook/notch 98', a loop of suture material (or string, for example) or a staple may be secured to the distal tip 96, 96' by tightening the loop into the groove 86 or hook/notch 98'. The inclusion of a coil electrode 92 and two sense electrodes 94 is merely illustrative of one lead electrode assembly that may be inserted with the aid of the methods/devices of the present invention.

FIG. 7 shows a perspective view of an insertion tool bending device. The bending device 100 includes posts 102 separated by a gap 104. To bend a device such as the shaft of the insertion tools 20, 40 shown in FIG. 2A-2B or 3A-3B, the shaft of the chosen device is passed through the gap 104 and turned with respect to the bending tool 100, allowing the posts 102 to reshape the device with a different curve. This may be done to match a chosen insertion tool more accurately to a patient's anatomy. The posts 102 may be modified by including caps, notches, grooves, hooks, overhangs or the like for retaining a device shaft going through the gap 104 to prevent it from slipping out.

FIG. 8 shows a perspective partial view of an infusion tubing set. The tubing set 110 may be used in conjunction with one of the insertion tools 20, 40 shown in FIG. 2A-2B or 3A-3B. The tubing set 110 is used to provide a flexible extension enabling easy attachment of a fluid infusion device to the Luer valve of a chosen insertion tool. The tubing set 110 includes first and second connectors 112, 114 and a flexible tubular shaft 116 therebetween.

FIGS. 9A-9B show, in combination and alone, an insertion tool with a splittable sheath and a splittable sheath by itself. FIG. 9A illustrates an insertion tool 150 having a handle 152 and a shaft 154 extending to a distal tip 156, with a splittable sheath 158 disposed thereon. The splittable sheath 158 is sized to snugly fit over the shaft 154, and is preferably shorter than the shaft 154 such that the distal end 156 can extend distally of the splittable sheath 158.

As further shown in FIG. 9B, the splittable sheath 158 has a proximal handle portion 160 and a distal end 162. The distal end 162 may be tapered or thinned such that there is no leading "shoulder" during insertion to tissue. Preferably, the splittable sheath 158 is thin enough that the distal end 162 of the splittable sheath 158 does not create significant drag during insertion, and does not require thinning, grinding, or the like.

Alternatively, though not shown in FIG. 9A, the insertion tool 150 may include a proximally facing lip near its distal end for seating the distal end of the splittable sheath 152. Such a proximally facing lip may be provided by preloading the splittable sheath 152 on the shaft and then providing an overlay or separate tip that can be secured (i.e., by heating, welding or adhesive) to the distal end of the shaft. In another embodiment (referring again to FIG. 9B), the distal end 162 of the splittable sheath 158 may be ground to smooth out the distal shoulder. The splittable sheath 158 also includes a region of longitudinal weakness 164 for splitting the handle 160, which also extends toward the distal end 162, allowing for splitting of the sheath itself.

Figure 10:
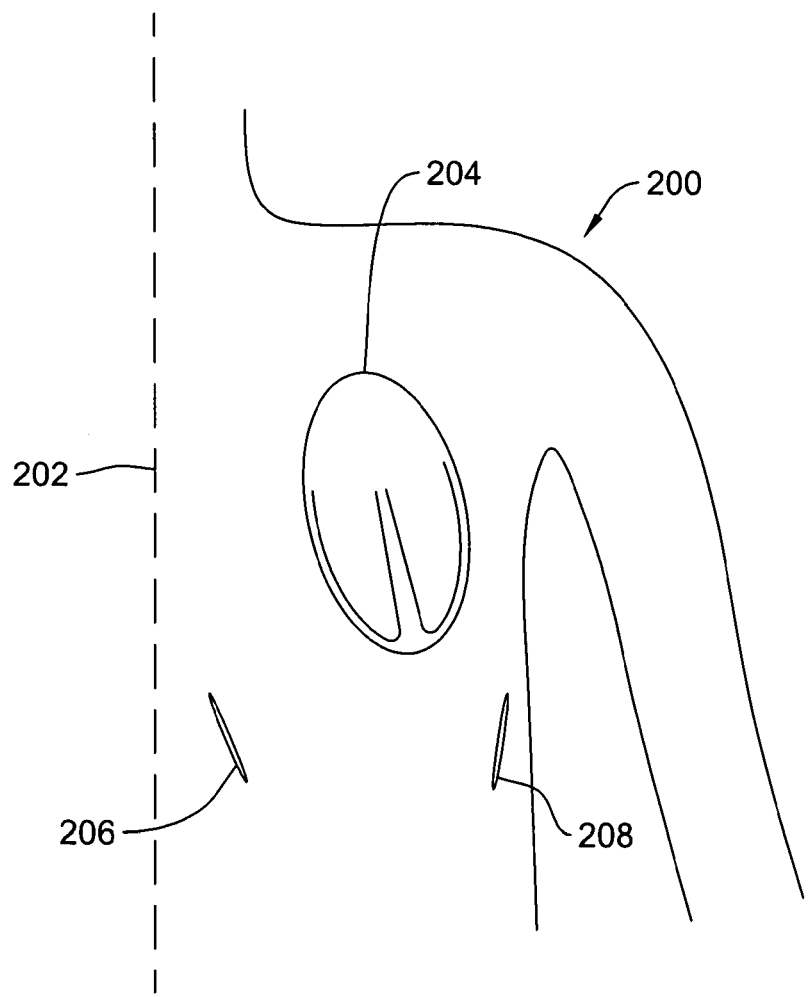
FIG. 10 shows a patient illustrating relative positions for illustrative incisions.

FIG. 10 shows a patient illustrating relative positions for incisions in an example procedure. The patient 200 is shown with the median plane 202 defined and a rough illustration of the heart 204 provided. Incision locations for a first incision 206 and a second incision 208 are shown, again as a relatively rough approximation. Preferably the incisions 206, 208 both lie over the same rib or between the same pair of ribs of the patient 200. Each incision is deep enough to enable subcutaneous access, but preferably does not extend further into patient 200. Such incisions may be made over any of the patients ribs, but are preferably made somewhere between the third and twelfth ribs of the patient. In another preferred embodiment, the line from the first incision to the second incision tracks, at least partly, the inframammary crease. The second incision is also preferably made in the region of the left anterior axillary line. While these are presently preferred locations, the specific locations of each incision may vary widely within the context of the present invention.

Figure 11A:
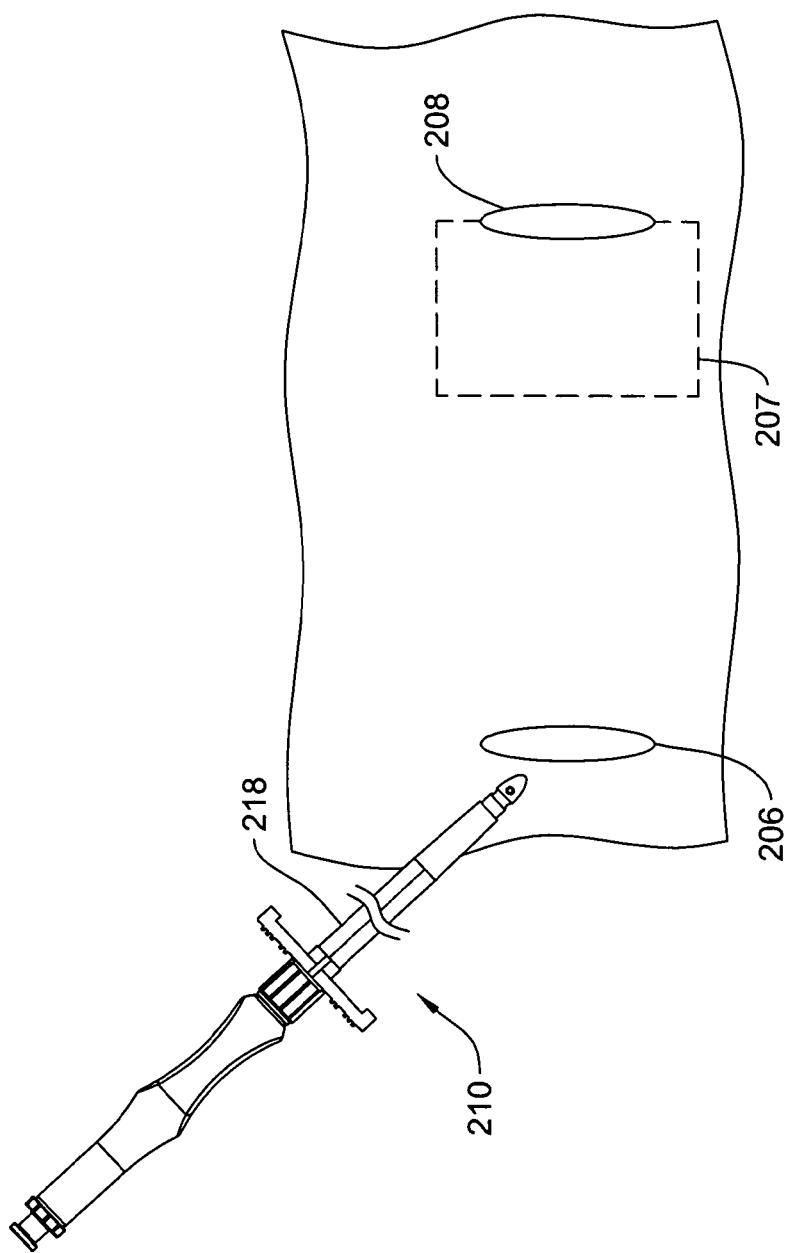
FIGS. 11A-11J show an illustrative method of electrode insertion.
Figure 11B:
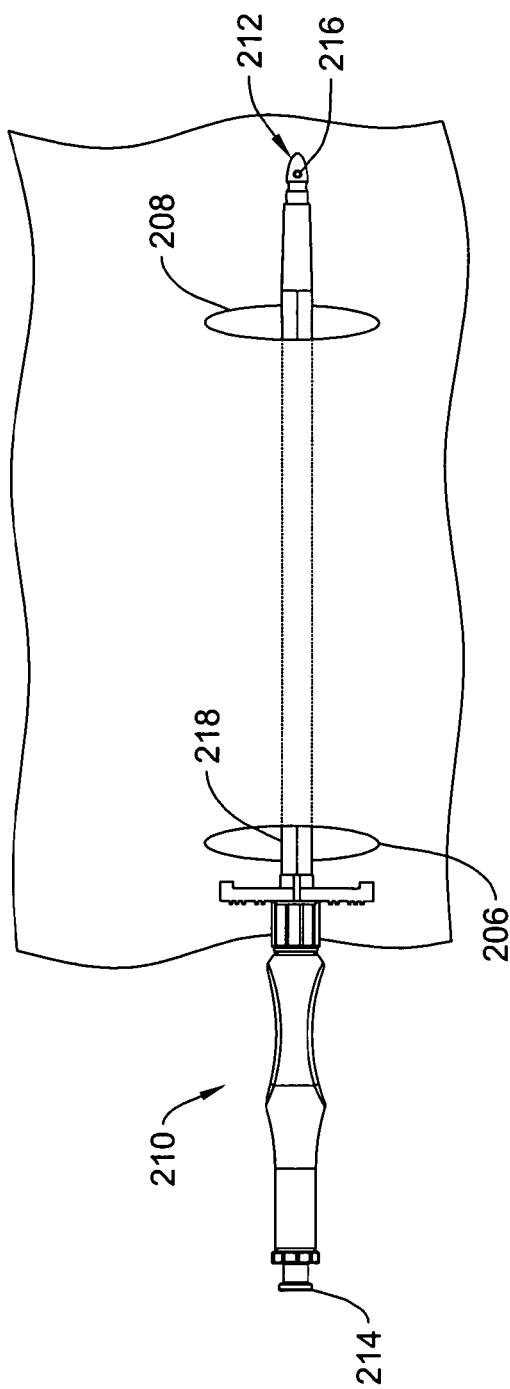

FIGS. 11A-11J show an illustrative method of electrode insertion. FIG. 11A illustrates a first step after the making of a first incision 206 and a second incision 208 in a patient 200. Note also that a pocket 207 has been defined in the subcutaneous region of the patient 200. The pocket 207 may be formed by inserting a trocar through the second incision and separating tissue layers with the trocar to define a subcutaneous pocket 207 or by using manual blunt dissection for receipt of an implantable device. An insertion tool 210 (illustrated as including a splittable sheath 218 thereon) is about to be inserted through the first opening 206. As shown in FIG. 11B, the insertion tool 210 is advanced from the first opening 206 toward and through the second opening, tunneling a path through the subcutaneous tissue along the way. While advancement of the distal end 212 through the second incision 208 is shown, this extent of insertion is not necessary. It is sufficient that the insertion tool 210 is advanced far enough to provide access from outside of incision 208 to the distal end 212 of the insertion tool 210 for access to an attachment feature. The attachment feature shown in FIG. 11B is shown, for illustrative purposes, as including a suture hole 216. During such insertion and tunneling, a local anaesthetic such as Lidocaine or the like may be supplied by infusion through a Luer hub 214 and passage through a lumen in the insertion tool 210.

Figure 11C:
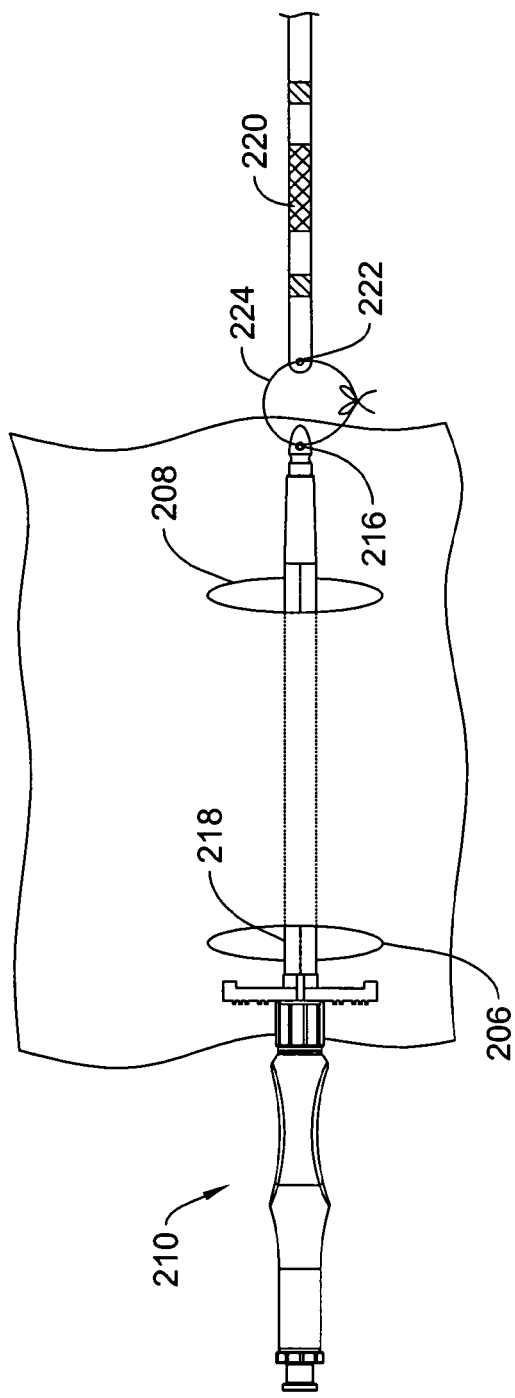

As shown in FIG. 11C, a next step includes attaching the distal end of a lead electrode assembly 220 to the distal end 212 of the insertion tool 210 using a suture loop 224 that passes through the insertion tool 210 suture hole 216 and a corresponding suture hole 222 on the lead electrode assembly 220. The illustrative lead electrode assembly 220 is shown having two sensing and one shocking electrode thereon; such a configuration is merely illustrative of one lead assembly, and use of the present invention need not be limited to such electrode lead assemblies.

Instead of suture holes 216, 222, other attachment features such as hooks or radial grooves, as illustrated above, may be used. Magnetic, screw-type, locking ball, snap fit, or other types of attachment may be substituted as well, though for the purposes of illustration, magnetic, screw-type, locking ball and snap fit attachment features have not been shown herein. It is sufficient that the attachment feature enable attachment of the insertion tool distal end to another element such as a lead electrode assembly. Advantageously, the suture holes, hooks or radial grooves allow for relatively simple and reliable attachment using readily available (and strong) suture material or staples. In particular, attaching a suture or staple is relatively simple. For sutures, any type of knot may be used, from simple slipknots to many stronger and more complex knots, to achieve a strong attachment. Removal is also simple, easy, and foolproof, being performed by merely cutting the suture/staple 224.

Figure 11D:
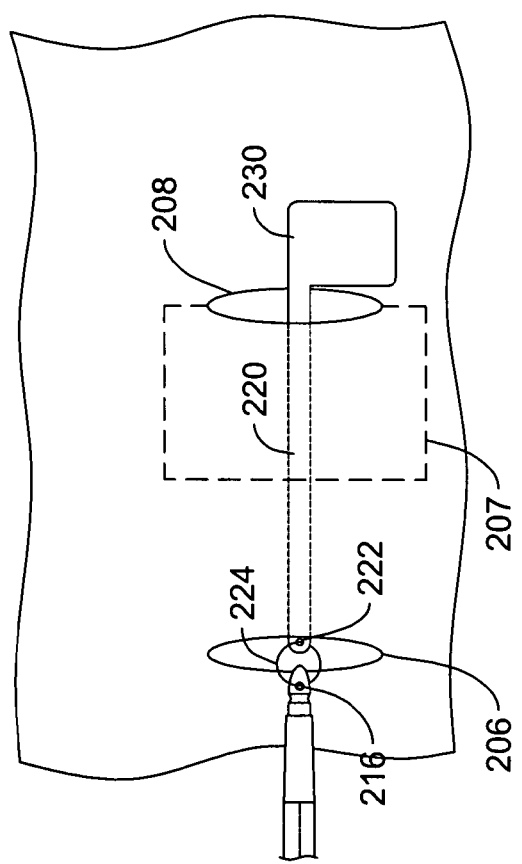

Referring now to FIG. 11D, a next step is illustrated wherein the insertion tool 210 is withdrawn through the first incision 206, pulling the lead electrode assembly 220 into the path tunneled by the insertion tool 210 between the incisions 206, 208 using the suture 224 and suture holes 216, 222. As shown, this step is performed until at least the suture 224 can be accessed from outside the patient.

In one embodiment of the present invention, the method may stop here. With the lead electrode assembly 220 pulled into the path between the incisions 206, 208, the lead assembly 220 may be sized such that a canister 230 attached to the proximal end of the lead electrode assembly 220 is pulled into the pocket 207. The suture 224 is then cut and the incisions 206, 208 sewn shut, such that implantation is essentially complete insofar as device placement is concerned. Because the lead assembly 220 is pulled into position after tunneling, rather than being carried or pushed into position, the resultant strains on the lead assembly 220 are reduced. Further, by advancing from a first incision 206 at a definite location to a second incision 208 at another definite location, both ends of the path so defined can be tightly controlled. Thus, placement inaccuracy is avoided.

Figure 11E:
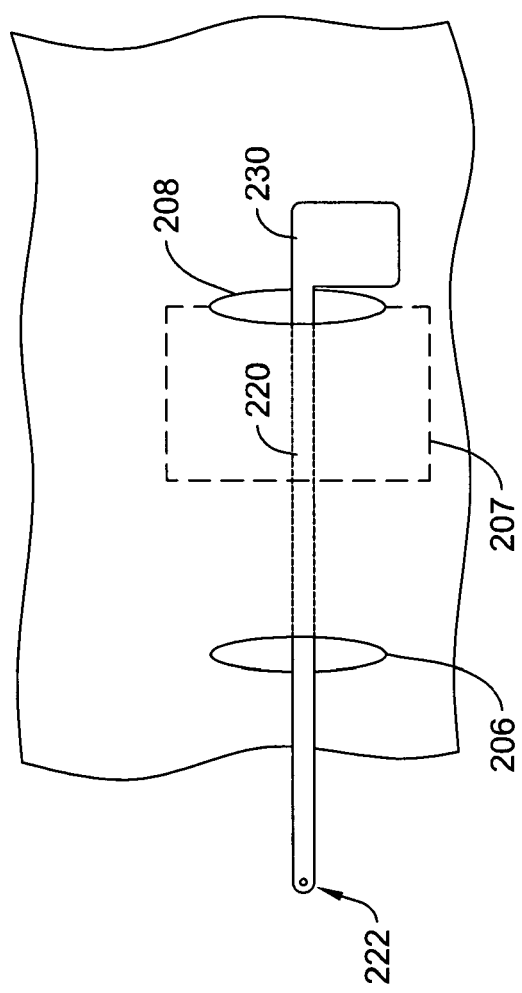
Figure 11F:
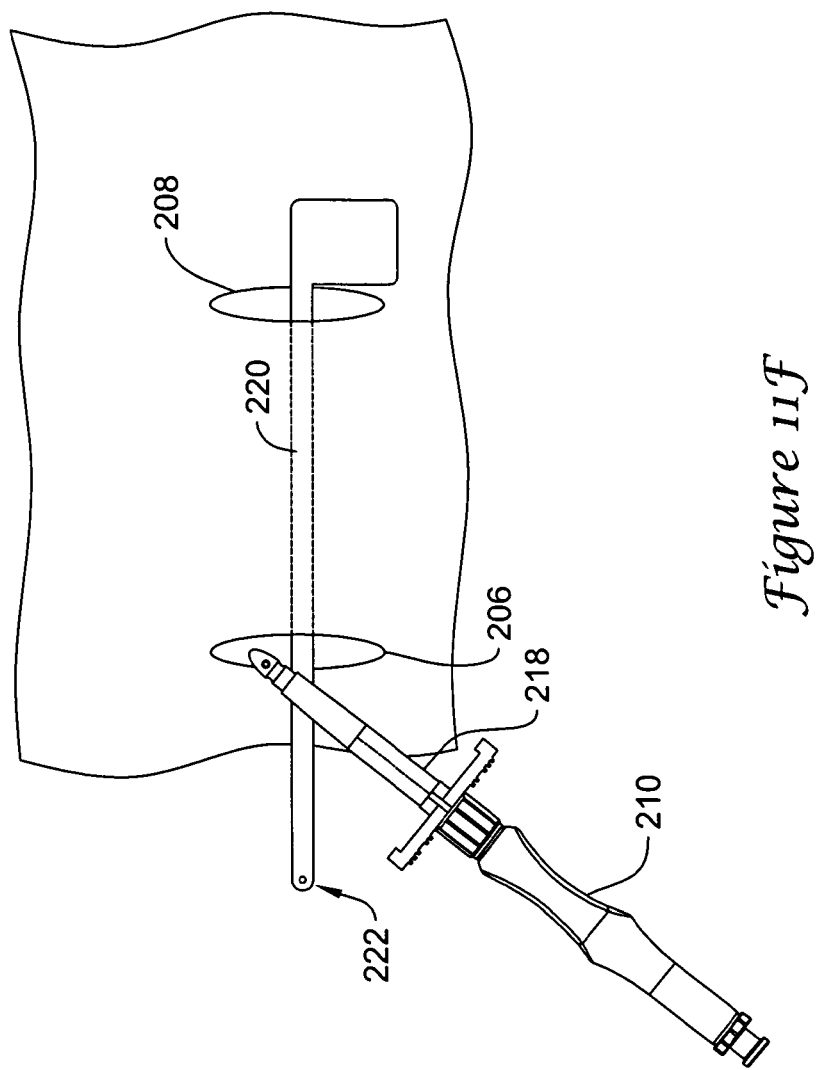

An alternative embodiment continues in FIGS. 11E-11J. After the step of FIG. 11D, as shown in FIG. 11E, the lead electrode assembly 220 is pulled for a greater distance allowing access to the distal end 222 thereof. The lead assembly 220 may be pulled sufficiently to cause it to exit the first incision 206 by a certain amount. Then, as shown in FIG. 11F, the insertion tool 210 with the splittable sheath 218 is re-inserted into the first incision 206, this time in a different direction than before. In an alternative embodiment, a first, preferably curved, insertion tool is used during the steps shown in FIGS. 11A-11E while a second, preferably straight, insertion tool is used in FIGS. 11F-11J, with the splittable sheath provided only for the straight insertion tool.

Figure 11G:
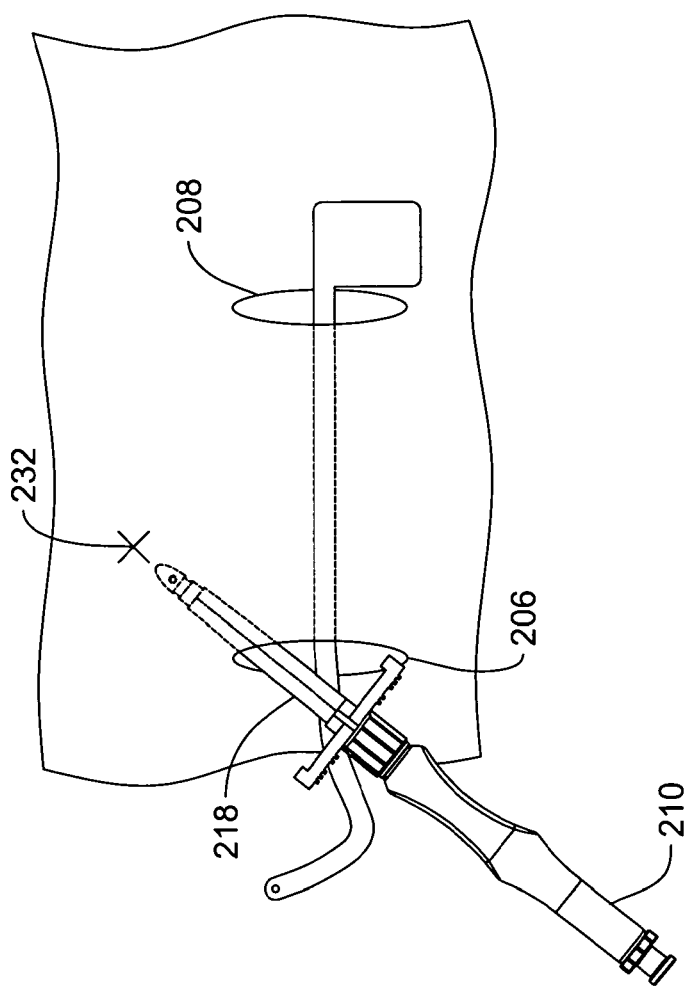

As shown in FIG. 11G, the insertion tool 210 is inserted via the first incision 206 toward a chosen point or location X 232 located cephalic (directed toward the head of the patient) of the first incision. Preferably, a line drawn from the first incision 206 to the second incision 208 is at an angle θ, between about 20 and 160 degrees, with respect to a line drawn from the first incision toward location X 232. More preferably, the angle θ is around about 90 degrees, being in the range of between 75 and 105 degrees.

Figure 11H:
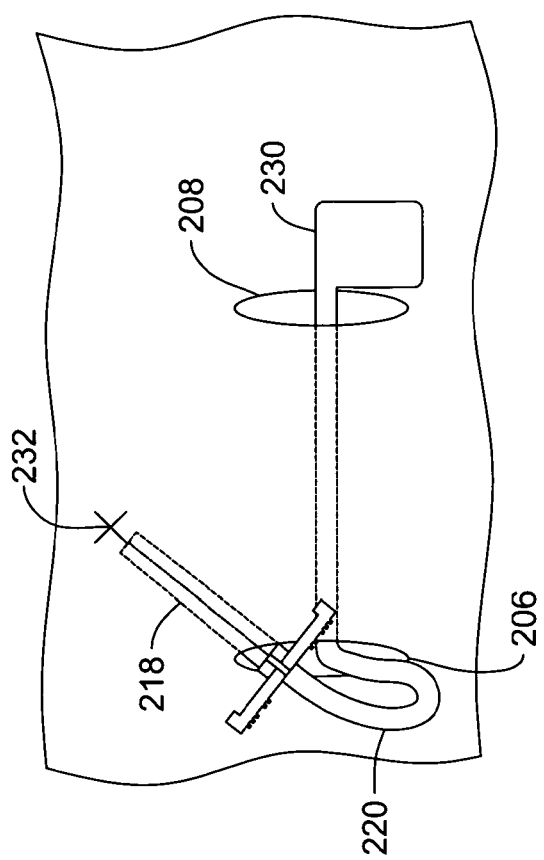
Figure 11I:
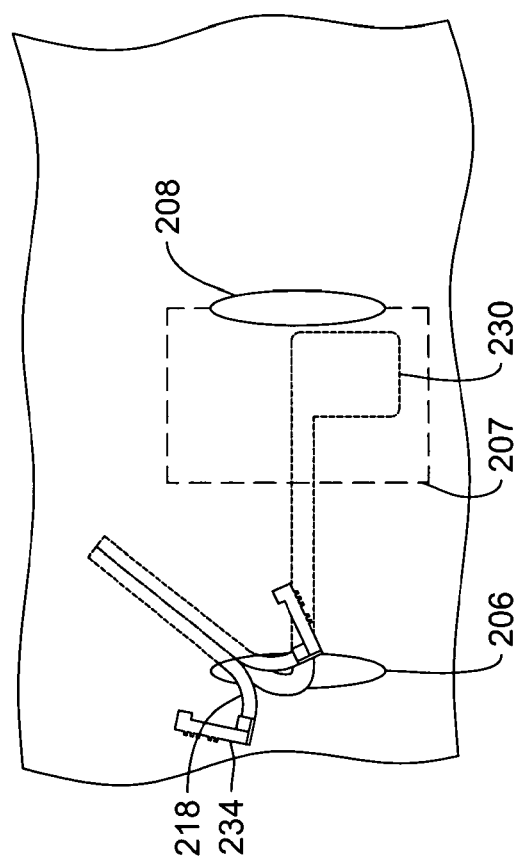
Figure 11J:
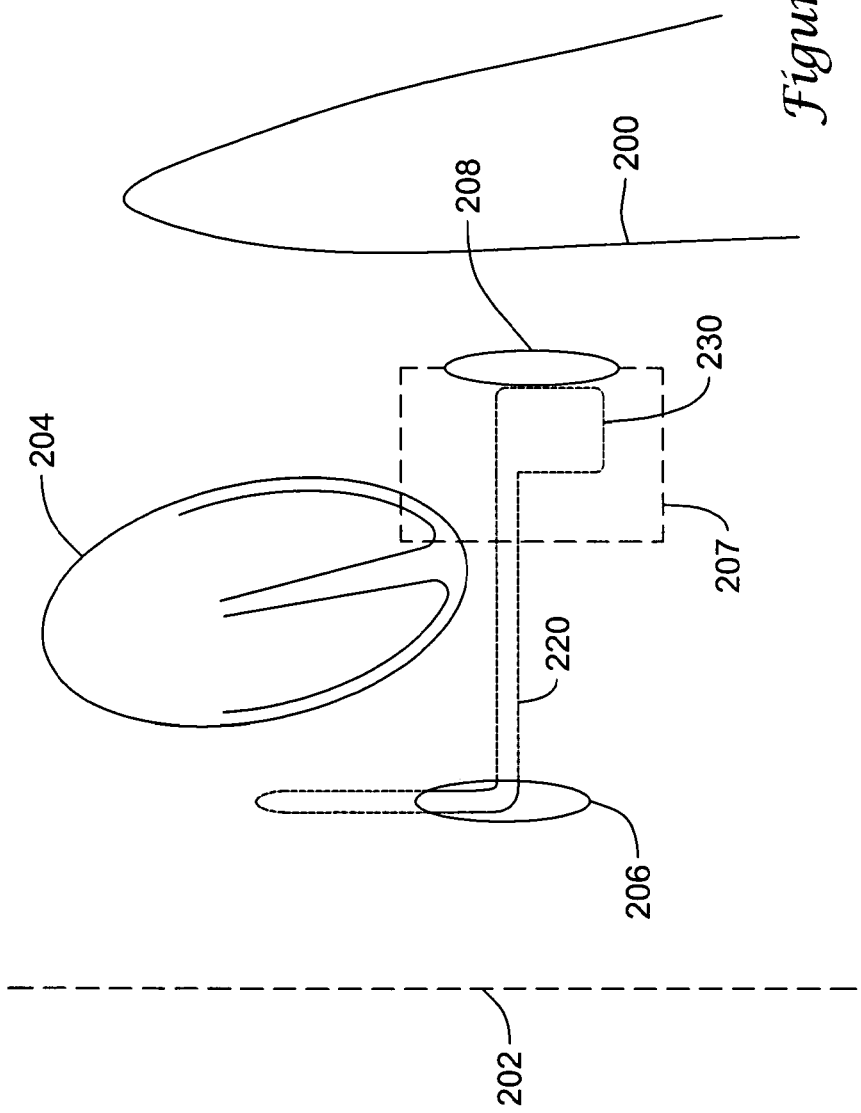

After the insertion tool 210 has tunneled a desired distance, and while the splittable sheath 218 may still be accessed from outside the patient, the insertion tool 210 is removed to leave the splittable sheath 218 in place, as shown in FIG. 11H. Next, the distal end of the lead electrode assembly 220 is directed into the splittable sheath 218, as also shown in FIG. 11H. Once the lead assembly 220 is directed into the splittable sheath 218 to a desired distance, the splittable sheath 218 may be removed by grasping handles 234 and tearing the sheath apart, as shown in FIG. 11I. At this point, as shown in FIG. 11I, the lead assembly 220 is preferably far enough into the patient longitudinally that the canister 230 has entered the pocket 207 and is inside the patient 200, through incision 208. As shown at FIG. 11J, the incisions 206, 208 are then closed, leaving the lead electrode assembly 220 and canister 230 fully implanted. After this point, the implantation is complete, and a variety of methods may be used to "activate" and/or program the canister 230 and whatever electronics for pacing and/or defibrillation are contained therein.

An advantage of the configuration for implantation of the electrode assembly shown in FIG. 11J is that the electrodes on the lead electrode assembly 220 are aligned in a new manner with respect to the canister 230. In prior art devices, the canister 230 was often generally collinear with the electrodes on the lead electrode assembly. An electrode on the canister 230 may be offset from the axial direction of the lead electrode assembly, allowing for some minor angular variation in exchange for reducing the distance between electrodes. Even if there were more than two sensing electrodes, the signals received by distinct sensing electrode pairs would have little variation, since collinear electrodes generally do not receive significantly different signals in the far-field, except for pairs that are close together and therefore yield poor signal anyway. The assembly inserted as shown in FIG. 11J enables multiple sensors on the distal end of the lead assembly 220, along with at least one canister electrode, to provide a wider variation in angular orientation, without closing the distance between the canister and the electrodes.

Figure 12A:
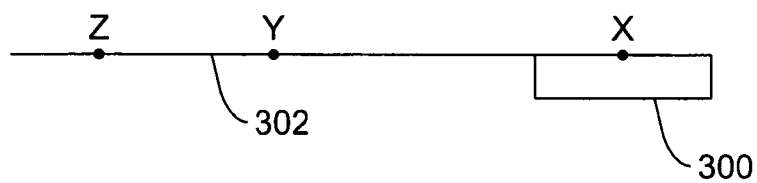
FIGS. 12A-12B illustrate several aspects of different sensor configurations.
Figure 12B:
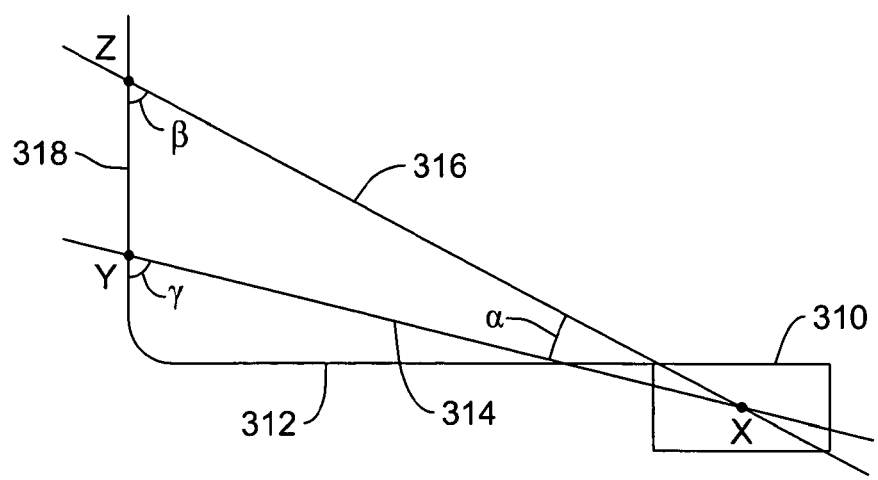

FIGS. 12A-12B help to further illustrate several relevant sensor characteristics. It should be recognized that, at least with far-field sensing of electrical activity in the heart, parallel sensor pairs tend to receive highly correlated signals. Over a short distance, there is little to be gained by having more than two sensors along the same line. Given a sensing lead electrode assembly and canister device as shown and oriented in FIG. 12A, dead signal sensing problems can arise.

Given sensor X on a canister 300, and sensors Y and Z on the lead electrode assembly 302, the primary difficulty arises when the need for backup sensing is greatest. In particular, if a minimal signal is sensed between a first sensor pair XY, a similarly minimal signal will be received by sensor pair YZ as well as signal pair XZ, since the three electrodes are collinear. If the minimal received signal is too close to the noise floor, then the sensors will fail to provide adequate data for reliable QRS detection, let alone sufficient information to provide pacing or defibrillating assistance. Even if X is offset from the line of the lead electrode assembly 302, the angular distinctions between pairs XY, XZ and YZ are quite small.

As shown in FIG. 12B, three sensors X, Y, and Z on a lead assembly 312 coupled to a canister 310 define three sensor pair vectors 314, 316, and 318 which have angles α, β, and γ therebetween. The above problem is avoided when the electrodes X, Y, and Z are not generally collinear, as shown. Angles α, β and γ are all relatively large, each being bigger than about fifteen degrees. If orthogonal sensing pairs are used, when the minimum signal is received by one of the pairs, a maximum signal is received by the other pair. While the vectors of XY, XZ and YZ are not exactly orthogonal, their deviation from being collinear is sufficient to eliminate the problems that arise with the configuration of FIG. 12A. When sensor backup is most needed (minimum signal received by one pair), the configuration or layout of FIG. 12B provides excellent backup.

In another embodiment (relying on another form of analysis), the insertion method is performed so that three sensors define a plane which at least partly intersects the heart. In yet another embodiment, sensors are placed so that at least one angle between sensor pair vectors is greater than 30 degrees. More preferably, at least one angle between sensor pair vectors is greater than about 60 degrees, while most preferably at least one angle between sensor pair vectors is in the range of about 70-90 degrees. Note that when referring to angles between sensor pair vectors, the angles referred to are the lesser angles between pairs of intersecting vectors. Another preferred layout is one in which the sine of the angles between sensing vectors is intentionally increased, preferably so that the sine of at least one such angle between sensing vectors is greater than or equal to about 0.5.

The layout of FIG. 12B illustrates only three sensors for the purpose of simplicity. It may be preferable to include four electrodes, with one canister electrode being both a sensing and a shocking electrode, while two lead electrodes are only sensing electrodes provided distal of and proximal of a shocking/sensing electrode coil. Indeed, unless specifically limited by the use of non-inclusive language in the following claims, the number of sensors used in a lead electrode assembly should not be understood as limiting the present invention.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of implanting an implantable defibrillator including a canister and a lead electrode assembly into a patient, the lead electrode assembly having proximal and distal ends, the method comprising:
    making an axillary incision near the left axilla of the patient and a xiphoid incision near the xiphoid of the patient;
    bluntly dissecting a pocket at the axillary incision for receiving the canister;
    advancing a first introducer tool having proximal and distal ends through the xiphoid incision toward the axillary incision to create a first subcutaneous tunnel, wherein the first introducer tool is curved to match patient anatomy between the xiphoid incision and the axillary incision;
    accessing the distal end of the first introducer tool via the axillary incision and securing the distal end of the lead electrode assembly to the distal end of the first introducer tool;
    withdrawing the first introducer tool through the xiphoid incision such that a portion of the lead electrode assembly is pulled through the axillary incision and into the first subcutaneous tunnel, until the first introducer tool fully exits the first subcutaneous tunnel and the distal end of the lead electrode assembly extends through the xiphoid incision while the proximal end of the lead electrode assembly remains outside of the first subcutaneous tunnel;
    inserting a second introducer tool, the second introducer tool being straight relative to the first introducer tool, through the xiphoid incision and toward the head of the patient along the sternum to create a second subcutaneous tunnel;
    removing the second introducer tool via the xiphoid incision; and
    inserting the distal end of the lead electrode assembly into the second subcutaneous tunnel.

2. The method of claim 1 wherein:
    during the step of inserting the second introducer tool, a splittable sheath is provided on the second introducer tool;
    during the step of removing the second introducer tool, the splittable sheath is kept in place in the second subcutaneous tunnel; and
    the lead electrode assembly is inserted into the second subcutaneous tunnel by insertion into the splittable sheath.

3. The method of claim 2 further comprising removing the splittable sheath by splitting the sheath along a line of weakness after the lead electrode assembly is inserted into the second subcutaneous tunnel.

4. The method of claim 3 further comprising:
    inserting the canister into the pocket; and
    closing the axillary and xiphoid incisions after the canister and lead electrode assembly are inserted.

5. The method of claim 1 further comprising:
    inserting the canister into the pocket; and
    closing the axillary and xiphoid incisions after the canister and lead electrode assembly are inserted.

* * * * *